(12) United States Patent
Bourlion

(10) Patent No.: US 8,486,119 B2
(45) Date of Patent: Jul. 16, 2013

(54) IMPLANT COMPRISING ONE OR MORE ELECTRODES AND CORRESPONDING INSERTION INSTRUMENT

(75) Inventor: Maurice Bourlion, Saint-Chamond (FR)

(73) Assignee: SpineGuard (FR)

( * ) Notice: Subject to any disclaimer, the term of this patent is extended or adjusted under 35 U.S.C. 154(b) by 397 days.

(21) Appl. No.: 11/660,418

(22) PCT Filed: Aug. 25, 2005

(86) PCT No.: PCT/FR2005/002143
§ 371 (c)(1),
(2), (4) Date: Apr. 12, 2007

(87) PCT Pub. No.: WO2006/024801
PCT Pub. Date: Mar. 9, 2006

(65) Prior Publication Data
US 2008/0045948 A1 Feb. 21, 2008

(30) Foreign Application Priority Data
Aug. 25, 2004 (FR) ..................... 04 09092

(51) Int. Cl.
*A61B 17/86* (2006.01)
(52) U.S. Cl.
USPC .......................................... 606/301

(58) Field of Classification Search
USPC .............. 606/300–321; 623/23.16, 23.49
See application file for complete search history.

(56) References Cited

U.S. PATENT DOCUMENTS

| 2,763,935 | A  | * | 9/1956  | Whaley et al. ................. 33/511 |
| 4,027,392 | A  | * | 6/1977  | Sawyer et al. ................ 433/174 |
| 6,030,162 | A  |   | 2/2000  | Huebner |
| 6,337,994 | B1 | * | 1/2002  | Stoianovici et al. .......... 600/547 |
| 6,391,005 | B1 | * | 5/2002  | Lum et al. ..................... 604/117 |
| 6,402,757 | B1 |   | 6/2002  | Moore, III et al. |
| 6,778,861 | B1 | * | 8/2004  | Liebrecht et al. ............ 607/116 |
| 2002/0183582 | A1 | * | 12/2002 | Green et al. ....................... 600/3 |
| 2003/0229354 | A1 |   | 12/2003 | Schmieding et al. |

FOREIGN PATENT DOCUMENTS

| DE | 34 14 992 A1 | 10/1985 |
| EP | 0 781 532 A2 | 7/1997  |
| FR | 2 835 732 A  | 8/2003  |
| GB | 2 356 051 A  | 5/2001  |

* cited by examiner

*Primary Examiner* — Michael T Schaper
(74) *Attorney, Agent, or Firm* — DLA Piper LLP (US)

(57) ABSTRACT

An implant for placement in an anatomical structure includes at least two electrodes separated by an insulator, the electrodes being flush with the surface of the implant to allow the implant to be followed up and guided during insertion in the anatomical structure.

23 Claims, 2 Drawing Sheets

IMPLANT COMPRISING ONE OR MORE ELECTRODES AND CORRESPONDING INSERTION INSTRUMENT

RELATED APPLICATION

This is a §371 of International Application No. PCT/FR2005/002143, with an international filing date of Aug. 25, 2005 (WO 2006/024801, published Mar. 9, 2006), which is based on French Patent Application No. 04/09092, filed Aug. 25, 2004.

TECHNICAL FIELD

The technology in this disclosure relates to the field of general orthopedics and, more particularly, to the insertion of implants, in particular implants such as screws, pins, etc., for placing devices that allow, for example, vertebral column correction and stabilization or fracture reduction.

BACKGROUND

Such implants are designed to be positioned in the bone structure.

One of the main difficulties practitioners find when inserting these implants is managing to position them correctly.

While incorrect positioning of the implant may not result in a satisfactory therapeutic result, it can also cause pain, paralysis, hemorrhages, etc. in the patient, which often require further surgical operations, or in certain cases can even cause irreparable damage.

It therefore becomes necessary for the practitioner to be able, not only to follow, but also to guide the implant during its insertion.

Devices that make it possible to follow the penetration of an instrument in an anatomical structure, in particular a bone structure, are known.

In particular, FR 2 835 732 provides a device that makes it possible to follow the penetration of a drilling instrument in the vertebra by measuring electrical impedance differences during penetration so that the practitioner can know, at all times, whether the tip of the instrument comes out of the bone cortex and penetrates a soft tissue area (marrow, nerves, tissue). In this case, the practitioner can modify the path of the penetration instrument to return to the bone cortex. Such a device makes it possible, therefore, to detect the formation of a crack in the bone cortex at the time of drilling the pre-drilling hole. For this purpose, the follow-up device comprises at least one electrostimulator capable of providing neuromuscular stimulation, which can be connected to at least two electrodes, at least one of which is located at one distal end of the drilling instrument, at least one inductometer connected to at least two electrodes, at least one of which is located at a distal end of the drilling instrument, and at least one signalling device capable of producing a signal in the event that the inductometer detects a change in the impedance.

Such a device does not, however, make it possible to follow up the insertion of an implant in the pre-drilling hole.

SUMMARY

This disclosure relates an implant for placement in an anatomical structure including at least two electrodes separated by an insulator, the electrodes being flush with the surface of the implant to allow the implant to be followed up and guided during insertion in the anatomical structure.

This disclosure also relates an implant for placement in an anatomical structure including at least one electrode that is flush with at least a part of a peripheral surface of the implant and a channel.

This disclosure further relates an insertion instrument for inserting an implant for placement in an anatomical structure including at least two electrodes separated by an insulator, the instrument being connected to a power source supplying at least two electrodes and to a means for measuring the impedance between the electrodes, including an internal longitudinal part housed in the channel of the implant, the longitudinal part consisting of an electrode.

BRIEF DESCRIPTION OF THE DRAWINGS

The disclosure will be understood better from reading the following description, provided for merely explanatory purposes, of a first embodiment, made in reference to the appended figures, wherein.

DETAILED DESCRIPTION

Figure 1:
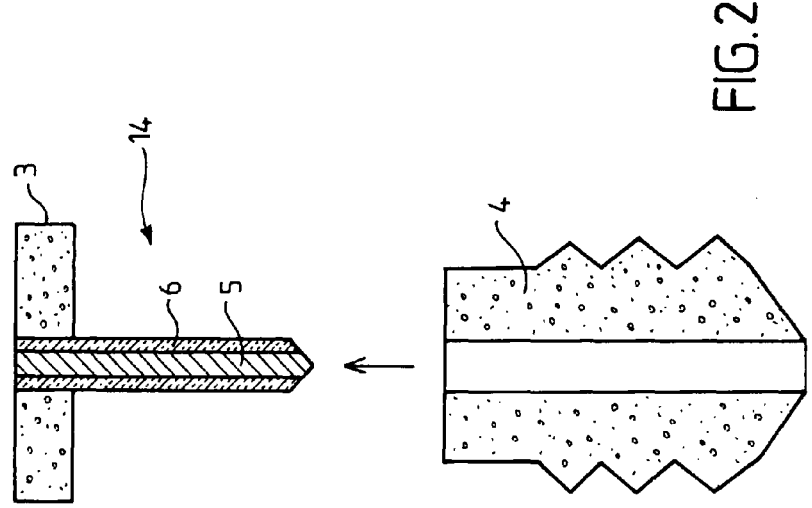
FIG. 1 shows a cross-section view of an implant.

I provide a piece of equipment that makes it possible to follow and guide an implant during its insertion in a bone structure, the latter being drilled directly by the implant during its insertion or during a previous operation.

For this purpose, I provide an implant intended to be inserted in an anatomical structure, in particular a bone structure.

The implant comprises at least two electrodes separated from one another by an insulator, the electrodes being flush with the surface of the implant to allow the implant to be followed up and guided during its insertion in the anatomical structure.

The electrodes are preferably arranged so that:
i) one of the electrodes is at least partially flush with the peripheral surface of the implant,
ii) the other electrode is selectively flush with the peripheral surface of the implant.

The electrodes are advantageously arranged so that:
i) one of the electrodes at least partially forms the peripheral surface of the implant,
ii) the other electrode, which is internal to the implant, is selectively flush with the distal surface of the implant.

With the implant thus configured, it is possible to follow its progress as it is inserted in the anatomical structure, when it is positioned using the adapted insertion instrument, which is described below.

The external electrode is preferably substantially tubular.

Likewise, the internal electrode is advantageously substantially tubular.

The electrodes are advantageously coaxial or eccentric.

In a preferred aspect, the electrode(s) can be removed.

The insulation is advantageously also removable. In this case, it is removed simultaneously with the internal electrode or once the latter has been removed.

I also provide an implant not equipped with the previously described removable part, namely the internal electrode and, optionally, the insulation. In this case, the implant, which has a channel passing through it, comprises at least one electrode being flush with at least a part of the peripheral surface of the implant, making up all or part of the lateral wall of the implant.

The implant preferably consists of a tubular electrode.

The implant advantageously comprises a tubular insulator.

The channel advantageously passes through the implant longitudinally.

The channel is advantageously a central channel.

I also disclose an insertion instrument intended for inserting the previously described implants in an anatomical structure, in particular in an anatomical bone structure. For this purpose, the instrument is connected to a power source supplying at least two electrodes and to a means for measuring the impedance between the electrodes.

In the case of an implant not equipped with the removable part as previously described, the instrument comprises an internal longitudinal part. This longitudinal part is designed to become housed in the channel of the implant. Depending on whether or not the implant is equipped with an insulator, the longitudinal part consists of an electrode or an electrode surrounded by an insulator.

The longitudinal part of the instrument is advantageously removable. Thus, without the longitudinal part, the instrument is adapted to be in contact with an implant which in turn comprises an internal electrode, separated from the external electrode by an insulator.

The instrument advantageously comprises means allowing electrical contact with the electrode or electrodes when the implant is in contact with the instrument. The electrical contact can be carried out internally and/or externally. Thus, for an internal contact, the insertion instrument comprises electrical contact elements positioned to be in contact with the internal electrode of the implant; for an external contact, the instrument comprises electrical contact elements positioned to be in contact with the peripheral electrode of the implant.

The instrument advantageously comprises a cavity for receiving part of the implant, as well as means that allow the implant housed in the instrument to be centered.

The insertion instrument advantageously comprises means for mechanically driving the implant.

With the implant and the instrument thus configured, it is then possible to follow the progress of the implant during its insertion in the bone structure by analysing an electric signal created by means of the electrodes.

When the distal end of the system, made up of the instrument and the implant, comes into contact with a crack formed in the bone structure, the impedance drops suddenly. With this information, the practitioner can rectify the path given to the implant to reposition it in the bone structure. The process continues in this way until the implant has been finally installed.

FIG. 1 shows a cross-section view of an implant (1) according to a first aspect.

The implant (1), such as a pedicle screw, has a threaded cylindrical body (2) having a pointed distal end (13), the other end being equipped with a head (3). The disclosure is not limited to this implant configuration, which was chosen in this case for its simplicity and therefore to facilitate the description of the implant.

The body (2) of the implant (1) comprises two conductive parts separated by an insulator (6).

More particularly, each of the conductive parts consists of an electrode (4, 5): a first electrode (4) forming the lateral wall of the implant (1) (external electrode) so that the external electrode is flush with the lateral surface (17) and a part of the distal surface (18) of the body (2) of the implant (1); a second electrode (5) constituting an internal part of the implant ("internal electrode") and being selectively flush with the distal surface (18) of the body (2) of the implant (1).

The internal electrode (5), in the shape of a rod with a circular cross-section, advantageously passes through the implant (1). It is surrounded by the insulator (6), which in turn is surrounded by the external electrode (4).

According to a preferred configuration, electrodes (4, 5) are arranged to be coaxial. This is a specific configuration, it being understood that the body (2) of the implant (1) can consist, for example, of two eccentric electrodes.

To facilitate the electrical contact with an instrument intended for inserting such an implant (2) in a bone structure, the internal electrode (5) and the insulator (6) are extended through the head (3) of the implant (1).

Figure 2:
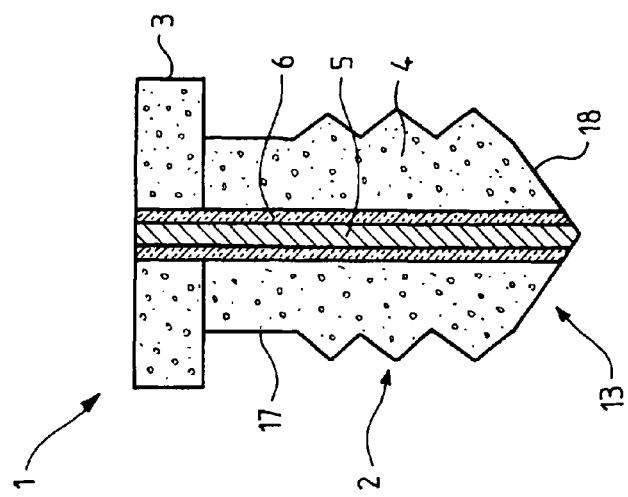
FIG. 2 shows a cross-section view of the implant of FIG. 1 having removed the removable part of the implant, as well as a cross-section view of the removable part removed from the implant.

According to a particularly advantageous the, the implant (1) comprises a removable part (14). In this way, when the removable part (14) is removed, generally once the implant (1) has been positioned in the bone structure, a channel is formed in the implant (1) following its longitudinal axis (see FIG. 2).

The removable part (14) preferably comprises both the internal electrode (5) and the insulator (6). However, it is evident that those skilled in the art will be able to plan for the removable part (14) of the implant (1) to consist only of the internal electrode (5), the insulator (6) remaining in the implant (1) when the removable part (14) is removed.

The removal of certain parts of the implant, such as the internal electrode and the insulator in the example described above, makes it possible to avoid leaving several types of material implanted in the patient's body.

In addition, since only the materials that remain in the body of the patient must necessarily be so-called "implantable" materials, the parts of the implant removed once the latter is disposed in the bone structure can be made entirely from biocompatible materials. Since biocompatible materials are less expensive than implantable materials, an implant comprising a removable part will thus have the advantage of having a lower manufacturing cost than an implant that does not have a removable part.

Figure 3:
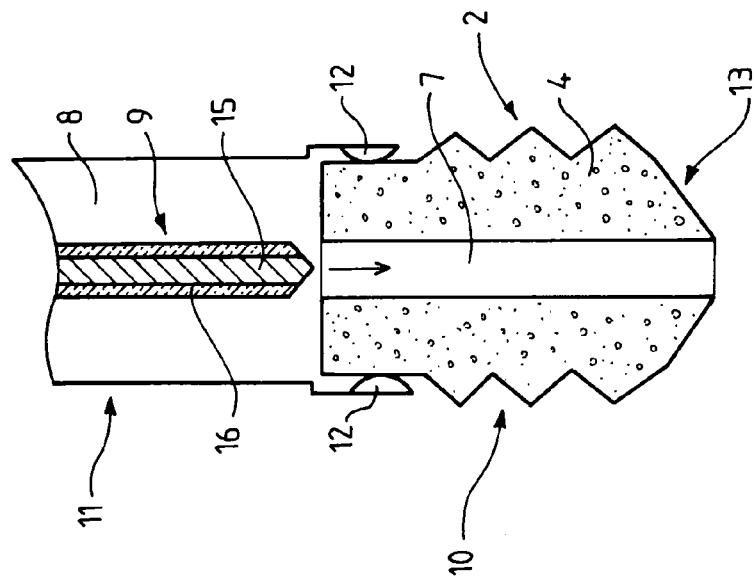
FIG. 3 shows a schematic view of an insertion instrument in contact with the implant of FIG. 1.

FIG. 3 shows a simplified view of the electrical contact between an instrument (11) for inserting an implant in a bone structure and the previously described implant (1). To simplify the figure, the real contact between the implant (1) and the instrument (11) has not been shown.

The electrical contact between the insertion instrument (11) and the implant (1) is provided by connection tabs (12, 19) which constitute the insertion instrument (11): an internal connection tab (19) being in contact with the internal electrode (5) of the implant (1) and at least one external connection tab (12) being in contact with the external electrode (4) of the implant (1).

In addition, since it is required to follow and guide the implant (1) during its insertion in the bone structure, the connection tabs (12, 19) of the insertion instrument (11) are connected to means for measuring the impedance between the electrodes (4, 5) (inductometer 20).

Inductometer (20) can advantageously be connected to a warning device (not shown) that makes it possible to view the impedance variations measured between the electrodes (4, 5) by the inductometer (20). This can be, for example, a display screen that allows the follow-up, in the form of curves, of variations in the impedance as the implant (1) penetrates in the bone structure.

Figure 4:
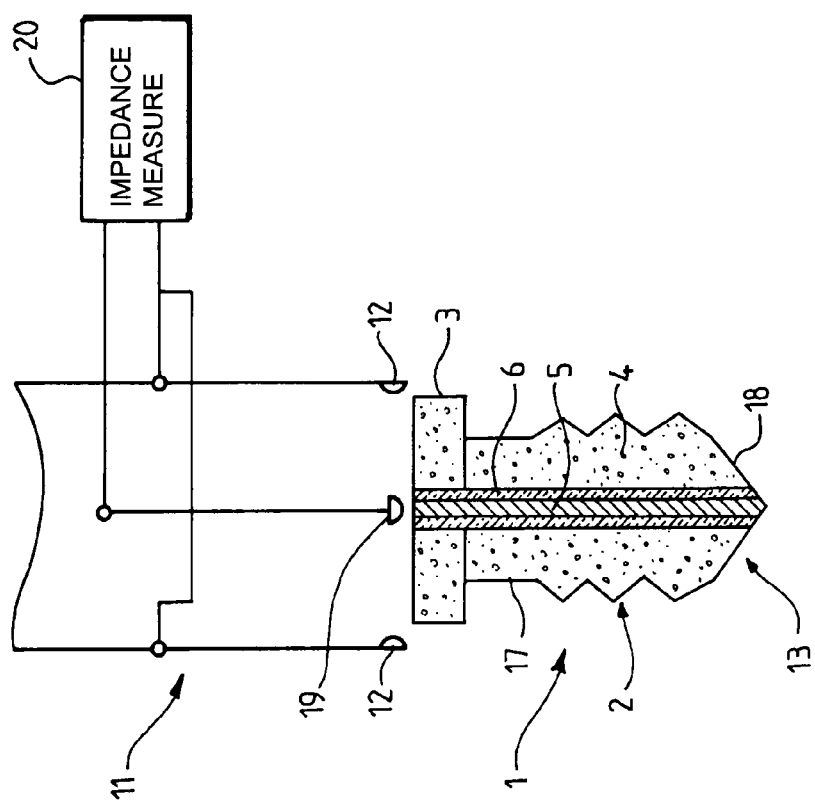
FIG. 4 shows a cross-section view of an implant according to another implant, the implant being in contact with an insertion instrument.

FIG. 4 shows a cross-section view of an implant (10) according to another configuration and of an insertion instrument (11) intended for placing the implant (10) in the bone structure.

To facilitate understanding of the principle of cooperation of the implant (10) with the instrument (11) and, in particular, to distinguish the elements that respectively make up the insertion instrument (11) and the implant (10), this figure does not show the real cooperation between the implant (10) and the instrument (11).

In this example, the implant (10) consists of a threaded conductive body (2) having a pointed distal end (13).

The tubular body (2) of the implant (10) is advantageously equipped with a channel (7) passing from one end of the body (2) of the implant (1) to the other.

The body (2) of the implant (10) is advantageously made up of an electrode (4).

Insertion instrument (11) intended for coming into contact with the implant (10) consists of a hollow body (8) equipped with a central longitudinal part (9), which is intended for becoming housed in the channel (7) of the implant (10) when the latter is in contact with the instrument (11).

Central longitudinal part (9) advantageously consists of an electrode (15) surrounded by an insulator (16). It is obviously evident that the longitudinal part (9) can consist of only the electrode (15), the implant intended for coming into contact with the insertion instrument (11) comprising its own insulator.

Thus, during its insertion in the bone structure, the implant (10) is fixed to the end of the instrument (11), and the longitudinal part (9) of the instrument (11) is inserted in the channel (7) of the implant (10).

Electrical continuity is established to follow up the progress of the insertion of the implant (10).

The electrical contact is advantageously provided by means of connection tabs (12) that come into contact with the electrode (4) constituting the implant (10).

Only the electrical part of the insertion instrument (11) that allows the follow-up and guiding of an implant in the bone structure has been presented. It is evident for those skilled in the art that the insertion instrument (11) can comprise mechanical driving means which can be manual or such as an electric motor, which make it possible, for example, to drive the rotation, thrust, etc. of the implant.

The disclosure is described in the preceding paragraphs by way of an example. It is evident that a person skilled in the art will be capable of producing different configurations without departing from the scope of the appended claims.

The invention claimed is:

1. An assembly comprising an implant for placement in an anatomical structure and an insertion instrument for inserting the implant in the anatomical structure, the implant having a proximal and distal end and comprising:
   at least an implantable part made of implantable material that is configured to remain in the anatomical structure, the implantable part having a threaded outer surface adapted to anchor the implant in the anatomical structure,
   a head on the proximal end of the implant that engages the insertion instrument;
   at least a first electrode and a second electrode that are flush with a peripheral surface of the implant, wherein the first electrode has a channel housing the second electrode; and
   an insulator separating the first and second electrodes, the insertion instrument comprising:
   means allowing electrical contact with the first and second electrodes when the proximal end of the implant is in contact with the insertion instrument,
   a power source supplying the first and second electrodes of the implant, and
   a device that measures impedance between the first and second electrodes of the implant to allow the implant to be followed up and guided during its insertion into the anatomical structure.

2. The assembly according to claim 1, wherein the electrodes are arranged so that:
   i) the first electrode is an external electrode that at least partially forms the peripheral surface of the implant,
   ii) the second electrode, which is internal to the implant, is an internal electrode that is selectively flush with a distal surface of the implant.

3. The assembly according to claim 2, wherein the external electrode is substantially tubular.

4. The assembly according to claim 2, wherein the internal electrode is substantially tubular.

5. The assembly according to claim 2, wherein the external electrode forms the implantable part.

6. The assembly according to claim 1, wherein the first and second electrodes are coaxial.

7. The assembly according to claim 1, wherein the first and second electrodes are eccentric.

8. The assembly according to claim 1, wherein part of the implant is removable once the implant has been placed in the anatomical structure.

9. The assembly according to claim 8, wherein the part of the implant that is removable comprises at least one of the first and second electrodes.

10. The assembly according to claim 8, wherein the part of the implant that is removable comprises the insulator.

11. The assembly according to claim 8, wherein the part of the implant that is removable is made of biocompatible material.

12. The assembly according to claim 1, further comprising a cavity for receiving part of the implant, as well as means that allow the implant housed in the instrument to be centered.

13. The assembly according to claim 1, comprising means for mechanically driving the implant.

14. An assembly comprising an implant for placement in an anatomical structure and an insertion instrument for inserting the implant in the anatomical structure, the implant comprising:
   at least an implantable part made of implantable material that is configured to remain in the anatomical structure, the implantable part having a threaded outer surface adapted to anchor the implant in the anatomical structure,
   at least a first electrode that is flush with at least a part of a peripheral surface of the implant, and
   a channel,
   the insertion instrument comprising:
   an internal longitudinal part comprising a second electrode and slidably receivable within the channel, the longitudinal part being housed in the channel of the implant with the second electrode flush with the peripheral surface of the implant when the implant is in contact with the insertion instrument,
   means allowing electrical contact with the first electrode when the implant is in contact with the instrument,
   a power source supplying the first and second electrodes, and a device that measures impedance between the first and second electrodes to allow the implant to be followed up and guided during its insertion into the anatomical structure.

15. The assembly according to claim 14, wherein the first electrode is tubular.

16. The implant assembly according to claim 14, further comprising a tubular insulator.

17. The assembly according to claim 14, wherein the channel passes through the implant longitudinally.

18. The assembly according to claim 14, wherein the channel is centrally located.

19. The assembly according to claim 14, wherein the second electrode of the insertion instrument is surrounded by an insulator.

20. The instrument assembly according to claim 14, wherein the longitudinal part of the insertion instrument is removable.

21. The assembly according to claim 14, further comprising a cavity for receiving part of the implant, as well as means that allow the implant housed in the instrument to be centered.

22. The assembly according to claim 14, comprising means for mechanically driving the implant.

23. The assembly according to claim 14, wherein the first electrode forms the implantable part.

* * * * *